(12) United States Patent
Kuntz

(10) Patent No.: US 6,702,815 B2
(45) Date of Patent: Mar. 9, 2004

(54) METHOD AND DEVICE TO CORRECT INSTABILITY OF HINGED JOINTS

(76) Inventor: Charles Kuntz, 6651 F Backlick Rd., Springfield, VA (US) 22150

( * ) Notice: Subject to any disclaimer, the term of this patent is extended or adjusted under 35 U.S.C. 154(b) by 0 days.

(21) Appl. No.: 10/196,194

(22) Filed: Jul. 17, 2002

(65) Prior Publication Data

US 2002/0183745 A1 Dec. 5, 2002

Related U.S. Application Data

(63) Continuation-in-part of application No. 09/987,022, filed on Nov. 13, 2001.
(60) Provisional application No. 60/250,142, filed on Dec. 1, 2000.

(51) Int. Cl.[7] .............................................. A61B 17/56
(52) U.S. Cl. .......................................... 606/60; 606/65
(58) Field of Search .............................. 606/65, 88, 60, 606/61, 62, 63, 54, 69, 70, 71, 86

(56) References Cited

U.S. PATENT DOCUMENTS

| | | |
|---|---|---|
| 4,246,660 A | 1/1981 | Wevers |
| 4,612,918 A | 9/1986 | Slocum |
| 4,677,973 A | 7/1987 | Slocum |
| 4,762,122 A | 8/1988 | Slocum |
| 5,458,601 A | 10/1995 | Young, Jr. et al. |
| 5,492,442 A | 2/1996 | Lasner |
| 5,520,689 A | 5/1996 | Schlapfer et al. |
| 5,527,315 A | 6/1996 | Jeanson et al. |
| 5,540,688 A | 7/1996 | Navas |
| 5,562,660 A | 10/1996 | Grob |
| 5,575,791 A * | 11/1996 | Lin ............................... 606/61 |
| 5,575,819 A | 11/1996 | Amis |
| 5,591,165 A | 1/1997 | Jackson |
| 5,591,166 A | 1/1997 | Bernhardt et al. |
| 5,601,554 A | 2/1997 | Howland et al. |
| 5,620,443 A | 4/1997 | Gertzbein et al. |
| 5,643,260 A * | 7/1997 | Doherty ........................ 606/61 |
| 5,658,283 A * | 8/1997 | Huebner ....................... 606/57 |
| 5,725,527 A | 3/1998 | Biedermann et al. |
| 5,728,127 A | 3/1998 | Asher et al. |
| 5,735,850 A * | 4/1998 | Baumgartner et al. ........ 606/61 |
| 5,752,953 A | 5/1998 | Slocum |
| 5,870,832 A | 2/1999 | Slocum |
| 5,928,234 A * | 7/1999 | Manspeizer ................... 606/61 |
| 6,007,535 A * | 12/1999 | Rayhack et al. ............... 606/57 |
| D433,641 S | 11/2000 | Slocum |

FOREIGN PATENT DOCUMENTS

| | | |
|---|---|---|
| FR | 2679439 | 1/1993 |
| WO | WO 83/00010 | 1/1983 |
| WO | WO/89/05614 | 6/1989 |

OTHER PUBLICATIONS

Brian S. Beale, DVM, Diplomate ACVS, "What's New In Anterior Cruciate Ligament Repair", Reprinted in 1999 North American Veterinary Conference Proceedings Abstract, pp. 1 and 2, 1999.

* cited by examiner

Primary Examiner—Pedro Philogene
Assistant Examiner—David A Bonderer
(74) Attorney, Agent, or Firm—Richard C. Litman

(57) ABSTRACT

A method and device to correct instability of hinged joints of injured animals. The device is a rectangular block having three threaded fixation pins. Two fixation pins are inserted in the non-rotating bone and secured in the block by setscrews. The third fixation pin is inserted in the rotating bone.

8 Claims, 2 Drawing Sheets

METHOD AND DEVICE TO CORRECT INSTABILITY OF HINGED JOINTS

CROSS-REFERENCE TO RELATED APPLICATIONS

This application is a continuation-in-part of application Ser. No. 09/987,022 filed Nov. 13, 2001, which further claims the benefit of U.S. Provisional Patent Application Serial No. 60/250,142, filed Dec. 1, 2000.

BACKGROUND OF THE INVENTION

1. Field of the Invention

The present invention relates generally to medical devices. More specifically, the invention is an orthopedic device for stabilizing articulations of body portions in humans and animals, and particularly to a method and device for correcting instability of a hinge joint in a minimum of time.

2. Description of the Related Art

Numerous devices have been made for improving the stability of injured parts of the body. Some of the most significant advances in the art have concerned the development of improved apparatus for protecting and supporting injured joints. However, none of the references herein described presents a method and/or device for correcting instability of articulations, wherein an extracapsular technique is used with fixation through the center of rotation, and wherein no implant is left in place once healing has been completed.

U.S. Pat. No. 4,246,660, issued on Jan. 27, 1981, to Henk W. Wevers, describes a prosthetic ligament device including an elastic element securable to the underlying bone structure by means of a quick release bayonet-type fitting which permits rotational movement during engagement at one end and a length adjusting means at the other end thereof.

U.S. Pat. No. 5,458,601, issued on Oct. 17, 1995, to Franklin A. Young, Jr. et al., describes an adjustable ligament anchor for attaching a ligament to a bone. The ligament anchor includes a housing having an exterior surface, an interior surface, an intra-articular end, and an opposite extra-articular end. The interior surface defines a bore that extends longitudinally through the housing, joining the ends.

U.S. Pat. No. 5,492,442, issued on Feb. 20, 1996, to Jeffrey I. Lasner, describes a bone screw having a helical thread with a constant outside diameter curling around a tapered core. The fine screw tip and thread at the tip of the screw can be inserted into a bone with minimal tearing or cracking of the bone.

U.S. Pat. No. 5,520,689, issued on May 28, 1996, to Johannes F. Schlapfer et al., describes an osteosynthetic fastening device, preferably in the form of a pedicle screw or a spinal column hook, having a channel in its upper section for receiving a support rod, and a retaining element which clamps the rod in the socket through a spherical contact element.

U.S. Pat. No. 5,527,315, issued on Jun. 18, 1996, to Jean-Francis Jeanson et al., describes a device for spinal osteosynthesis, which includes an elongated bar having two parallel, spaced, longitudinal slots extending parallel to the bar length. The slots define a central bar branch and two side bar branches flanking the central branch. A plurality of fasteners extend from the bar. Each fastener has a shank to be implanted. A head is provided at an end of the shank. A groove is provided in the fastener head.

U.S. Pat. No. 5,540,688, issued on Jul. 30, 1996, to Fernand Navas, describes an intervertebral stabilization device made in the form of a damper adapted to resist elastically. On the one hand, there is an elongation and, on the other hand, an axial compression without buckling, as well as of at least two implants anchored on two adjacent vertebrae.

U.S. Pat. No. 5,562,660, issued on Oct. 8, 1996, to Dieter Grob, describes an apparatus for stiffening and/or correcting part of the vertebral column including at least two screw-shaped retaining devices, each of which is fixed to one of the vertebrae in the affected part of the vertebral column.

U.S. Pat. No. 5,575,819, issued on Nov. 19, 1996, to Andrew Amis, describes an artificial ligament for connecting across a skeletal joint, including a bundle of fibers, each bundle being made up of a plurality of filaments of polyethylene terephthalate. Also disclosed is a ligament fixation device in the form of a cylindrical grommet, and a tensioning instrument for use in implanting an artificial ligament.

U.S. Pat. No. 5,591,165, issued on Jan. 7, 1997, to Roger P. Jackson, describes a device having a connection element between a rod, or other longitudinal implant, and a bone anchorage screw in the degenerative vertebra. This connection element includes a ring so dimensioned that the rod is capable of extending therethrough. The ring is provided with screws for clamping to the rod and is radially extended by a cylindrical arm adapted to be secured to the bone anchorage screw and to be clamped on the screw.

U.S. Pat. No. 5,591,166 issued on Jan. 7, 1997, to Andrew Bernhardt shows an orthopedic bone bolt and bone plate construct including a bone plate member with open portions and a series of multi-angle fasteners attachable to the bone plate member at the open portions.

U.S. Pat. No. 5,601,554, issued on Feb. 11, 1997, to Robert S. Howland et al., describes a branch connection for spinal fixation systems. The connector comprises a cross brace, upper saddles and connectors for connecting the upper saddles and cross brace to the first and second spine rods to thereby cross brace the first and second spine rods. Lower saddles are integrally formed at opposite ends of the cross brace to mate with the upper saddles in gripping the spine rods.

U.S Pat. No. 5,620,443, issued on Apr. 15, 1997, to Stanley Gertzbein et al., describes an anterior screw-rod connector device comprising a transverse fixator assembly for spanning between a number of longitudinal members situated adjacent a patient's vertebrae, and methods for fixation of the spine which allow for variation of the distance between two or more vertebrae.

U.S Pat. No. 5,725,527, issued on Mar. 10, 1998, to Lutz Biedermann et al., describes an anchoring member comprising a shaft to be fastened to a bone and a head for connection with a rod. The head has a substantially U-shaped cross-section and is connected with the shaft at the base thereof. The head further includes two free legs defining a channel for receiving the rod.

U.S. Pat. No. 5,728,127, issued on Mar. 17, 1998, to Marc A. Asher et al., describes an apparatus for maintaining vertebrae of a spinal column in a desired spatial relationship comprising a longitudinal member extendable along the spinal column. A fastener and a staple connects the longitudinal member to a vertebra.

U.S. Pat. No. 5,735,850, issued on Apr. 7, 1998, to Walter Baumgartner et al., describes a fastening system for pedicel screws anchorable in different vertebra. The spherical screw heads lie in spherical shells of apertured counterbodies. The counter-bodies have planar support surfaces which lie on a supporting link in the region of elongate holes.

International Patent Application No. WO 83/00010, published on Jan. 6, 1983, for Jules S. Shapiro, describes a method of fixation of two bone portions, including the steps of holding the bones together, placing a powder fastening device over the bone portions, and activating the fastening device to drive a fastener into the bone portions.

International Patent Application No. WO 89/05614, published on Jun. 29, 1989, for Jean Collomb, describes a synthetic ligament for knees made of a biocompatible material, including an active ligamentary part arranged between the femoral and tibial regions of intra-articular penetration.

French Patent Publication No. 2,679,439, published on Jan. 29, 1993, for Philippe Lepinay describes a quadrilaterally-shaped device for the consolidation and replacement of a ligament.

U.S. Pat. No. 4,612,918 issued on Sep. 23, 1986, to Barclay Slocum describes a method of eliminating canine cauda equina syndrome to reduce or eliminate the pinching of nerves between the last or seventh lumbar vertebrae $L_7$ and the first sacral vertebrae $S_1$ by separating and fixing $L_7$ and $S_1$.

U.S. Pat. No. 4,677,973 issued on Jul. 7, 1987, to Barclay Slocum describes a proximal tibial osteotomy method for leveling a tibial plateau comprising cutting free the portion of the metaphysis of the tibia from the remaining lower portion with a cylindrical cut which has a curvature axis that is perpendicular to the sagittal plane. The cut proximal portion is rotated relative to the lower tibia portion and pinned.

U.S. Pat. No. 4,762,122 issued on Aug. 9, 1988, to Barclay Slocum describes a device and method for performing a pelvic osteotomy operation by utilizing a fixation bracket including dual planar plate members joined rigidly at their marginal edges by a web member which makes possible the fixation of ilial sections in desired angular and positional relationship.

U.S. Pat. No. 5,752,953 issued on May 19, 1998, to Barclay Slocum describes a device and method for adjusting a long-bone conformation to correct the varu, valgus, internal, and external rotation in one proximal tibial osteotomy operation. A jig having an elongated body with rotatable pins at each end is used to fix the separated bones.

U.S. Pat. No. 5,870,832 issued on Feb. 16, 1999, to Barclay Slocum describes a frame for positioning an elongate gravity-actuated measuring device such as a goniometer adjacent two three-dimensional objects to measure the angle between two objects, and includes first and second members. The first member is joined to, and extends away from such instrument, and is positionable against a surface of one of such objects. The second member is joined to, and extends away from such instrument, is spaced from the first member a preselected distance, and is positionable against a surface of the other object.

Design Patent No. 433,641 issued on Nov. 14, 2000, to Barclay Slocum describes a goniometer frame for holding a goniometer to measure angles.

A publication by Brian S. Beale, DVM, Diplomate ACVS, "What's New In Anterior Cruciate Ligament Repair", Reprinted in 1999 North American Veterinary Conference Proceedings Abstract, pp. 1 and 2, 1999. Surgical repair of the cranial cruciate-deficient stifle may take many forms. The vast number of surgical procedures developed to return stability to the unstable stifle suggests that no technique is ideal. The technique selected is often based on the age and weight of the patient, duration of injury and the surgeon's preference. The preference is to repair small dogs, i.e., less than 35 lbs., with a modified retinacular imbrication technique and larger dogs with a modified retinacular imbrication technique or an intracapsular procedure using either an autograft or a prosthetic ligament. The tibial plateau leveling technique is a relatively new technique that also shows potential for treating large dogs with anterior cruciate ligament repairs.

None of the above inventions, patents and publication taken either singularly or in combination, is seen to describe the instant invention as claimed. Thus, a method and device to correct instability of hinged animal joints in a minimum of convalescence time and solving the aforementioned problems is desired.

SUMMARY OF THE INVENTION

The present invention is directed to an orthopedic device for stabilization of damaged hinge joints, and includes fixed and rotating rigid bone members connected by an elongated rectangular block having three threaded pins. A pair of threaded pins is fixedly positioned in the upper fixed bone, and the third threaded pin is positioned in the lower rotating bone to reduce the luxation but allow free rotation. The pair of fixedly threaded pins is immobilized in the block by separate set screws.

The process of applying the device to an injured animal involves the following steps. The animal is placed in a dorsal recumbency with the injured leg hung. A limited approach is performed on the medial aspect of the tibio-tarsal bone to allow only enough exposure to determine the center-of-rotation from medial to lateral. A non-threaded pin is passed at the center-of-rotation from medial to lateral. The non-threaded pin is replaced with the block and the enhanced profile end-threaded pin without a setscrew. The tibio-tarsal joint is reduced to minimize joint space. Non-threaded pins are placed through the other two holes of the block and into the distal tibia. The block and pins are removed, and threaded tibial pins replace the non-threaded pins. The device is installed in place with the setscrews tightened for the adjacent pair of pins. Post-operative radiographs are performed to document the positions of the fixation pins. A soft-padded bandage is placed on the injury to manage concomitant soft-tissue injuries. Usually, after weekly rechecks and four weeks, the block is removed, but not the fixation pins under sedation to assess stability of the joint. If adequate stabilization has been achieved, the fixation pins are removed, and a soft padded bandage is added. The device and method of use can be applied to other hinge joints such as the shoulder, elbow, carpus, and stifle.

Accordingly, it is a principal object of the invention to provide a device and method for correcting instability of hinged animal joints.

It is another object of the invention to provide a block device having only three aligned pins.

It is a further object of the invention to provide a block device having three threaded pins with one pin separated by a greater distance from the other two adjacent pins to provide rotation of the rotatable limb.

Still another object of the invention is to a block device having the two adjacent pins in the non-rotatable limb secured in the block by setscrews.

It is an object of the invention to provide improved elements and arrangements thereof for the purposes described which is inexpensive, dependable and fully effective in accomplishing its intended purposes.

These and other objects of the present invention will become readily apparent upon further review of the following specification and drawings.

DETAILED DESCRIPTION OF THE PREFERRED EMBODIMENT

Figure 1:
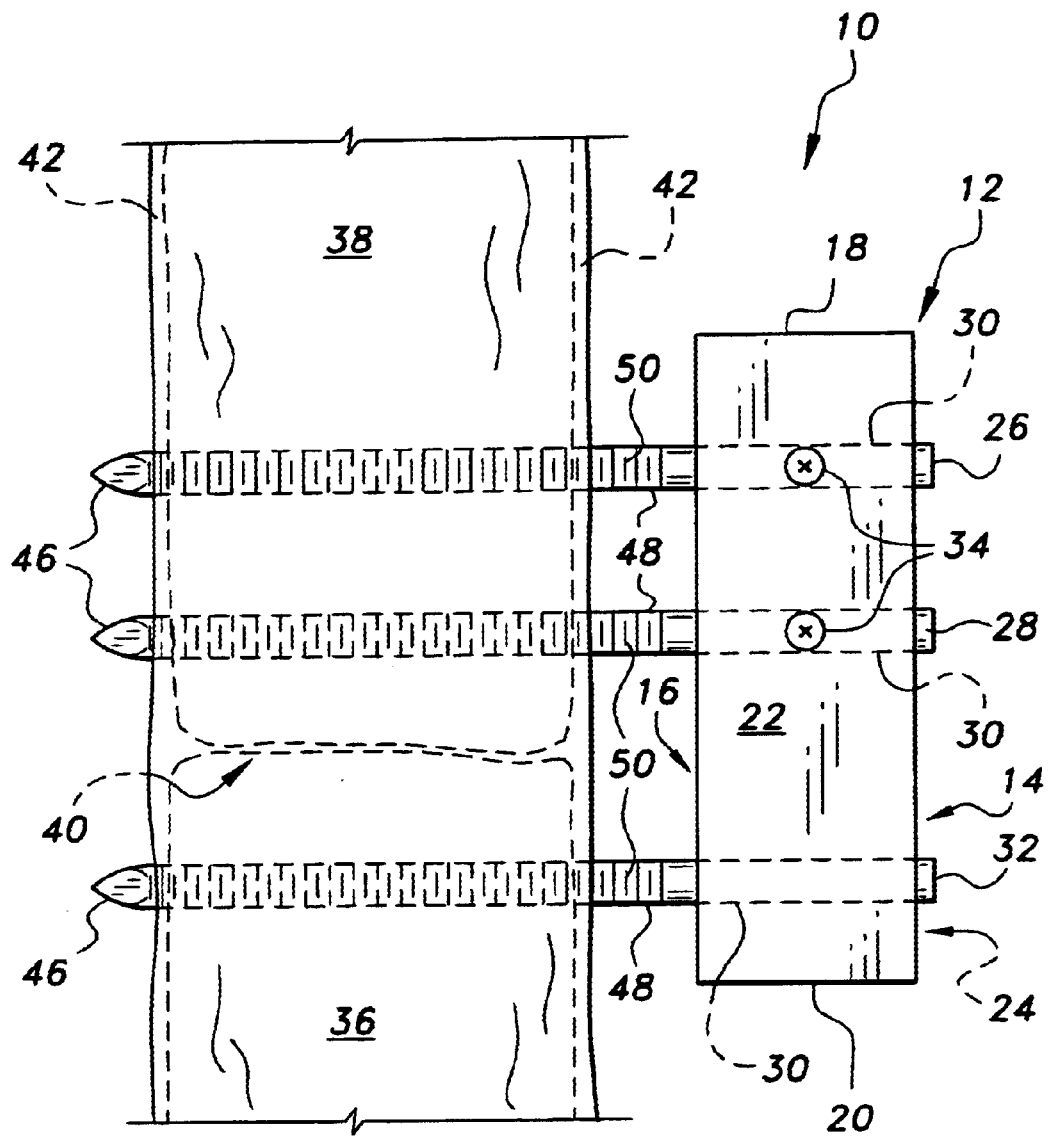
FIG. 1 is a schematic, environmental, side elevational view of a device to correct instability of hinged animal joints such as a leg according to the present invention.

The present invention is directed to a medical device useful for correcting the instability of an animal's hinged leg joint and to the device as depicted in FIG. 1 as an orthopedic fixation device 10.

Ligamentous injuries in hinge joints, particularly the collateral ligaments of the elbow and wrist in humans, and the hock or tarsal joint in digitigrade quadruped animals, together with prolonged immobilization often significantly result in permanent arthritis. The present invention counteracts this problem by allowing continued range of motion of the damaged hinge joint and reduces the incidence of arthritis.

It should be emphasized that a longfelt need exists for a more effective way of correcting instability in many kinds of joints, both large and small. The present invention is response to this need and, when in place, such as shown in FIG. 1, can be used to prevent the displacement of many different types of associated skeletal structures. It should be understood that other surgical approaches can be used with the orthopedic device 10, depending on the needs of the patient and the type of joint.

Figure 2:
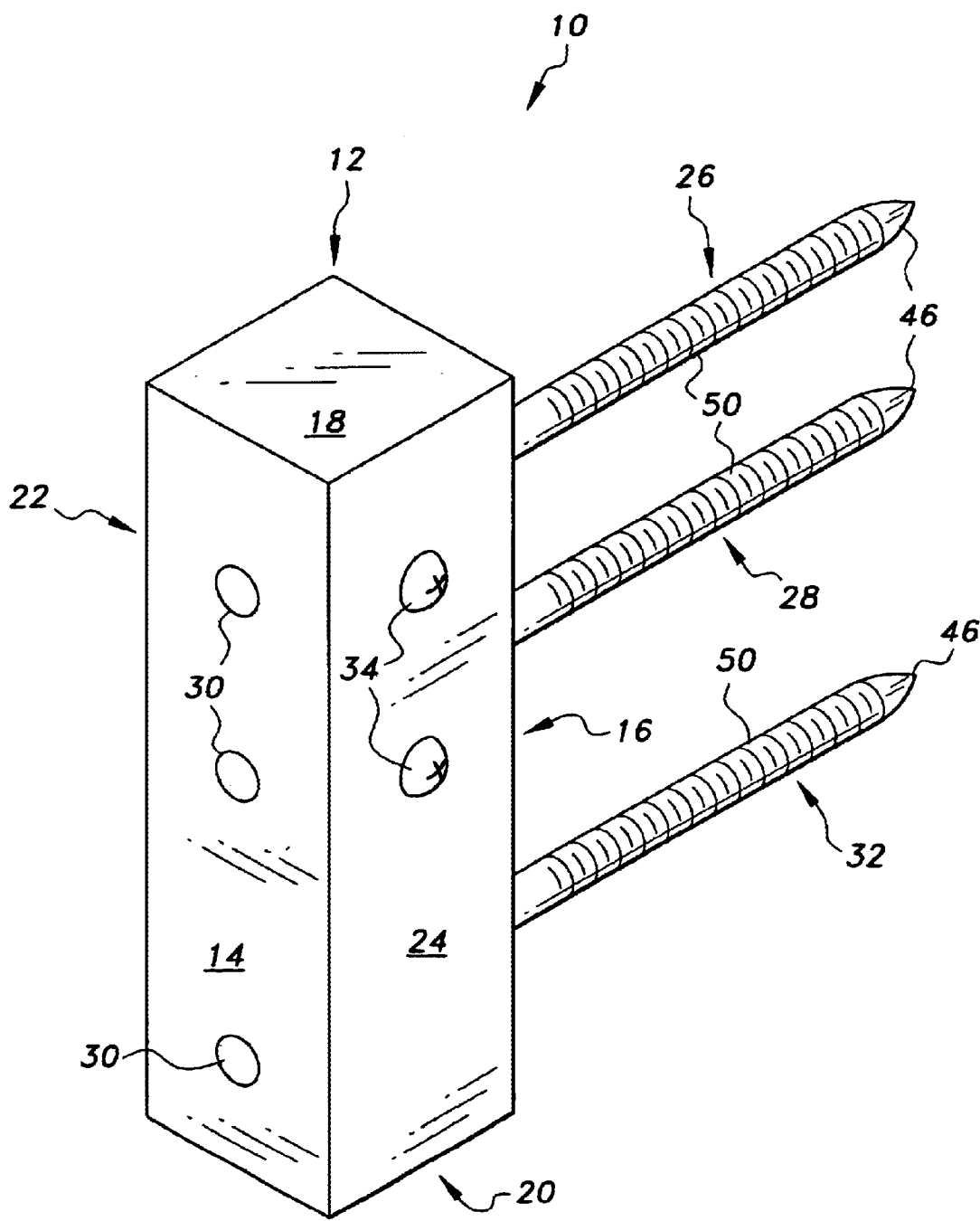
FIG. 2 is a perspective view of the FIG. 1 device.

In the schematic drawing of FIG. 1 and FIG. 2, the orthopedic fixation device 10 comprises a rectangular block 12 having rectangular top and bottom planar opposite surfaces 14 and 16, respectively, two planar opposite end square surfaces 18 (upper) and 20 (lower), respectively, and two planar, rectangular opposite side surfaces, 22 and 24 (hidden), respectively. A first threaded pin 26 and an adjacent second threaded pin 28 intersect the block 12 from the top planar surface 14 to the bottom planar surface 16 through throughbores 30.

A third threaded pin 32 spaced from the first and second threaded pins 26, 28 intersects the block 12 from the top surface 14 to the bottom surface 16 thereof.

The first and second pins 26, 28 are secured by fasteners 34 such as setscrews made of non-corrosive metal such as stainless steel or chromium plated steel from the front side surface 22. The third pin 32, therefore, is allowed to pivot in the block 12 and permit rotation of the lower bone or talus 36 relative to the upper bone or tibia 38 at the hinged joint 40. Reference number 42 represents the skin tissue. Cartilage has not been shown for simplification. Thus, two neighboring bones 36, 38 of the hinged joint or tibia-tarsal 40 can be connected by this medical device 10.

As previously noted, rupture of ligamentous structures causes joint instability. After placement of the device 10, scar tissue builds up over time to form a structure which mimics the function of the damaged ligament. This mass of scar tissue prevents abnormal motion from occurring. It has been found empirically that the present device 10 stabilizes joints more effectively than any other device, method or procedure previously employed, and without limiting the range of motion, principally, because the single end-threaded pin 22 is coincident with the center of rotation of the rotating member or bone 36 such as the talus relative to the center-of-rotation bone 38 such as the tibia.

The fixation pins 26, 28 and 32 are generally of elongated cylindrical shape having a distal pointed shaft end 46. The shaft 48 includes a threaded outer surface 50 configured so as to be implantable in the conventional surgical manner into a patient's bony tissue. Pins of various types such as commonly known in the art can be used. Additionally, the block 12 is preferably made of a polymeric material such as TEFLON (™), but aluminum or stainless steel can be used. It should be noted that the block 12 can have rounded edges to prevent irritation.

A general method of using the device 10 is as follows. A surgical incision in the hinge joint region is performed, allowing for joint exploration (partial or complete) if required, and excision or repair of the ligament remnants. A single enhanced profile-end threaded fixation pin 32 is placed at the center of rotation of the tibia. Pins 26 and 28 are passed through the throughbores 30 of the block 12 and driven into the tibia 38. The talus 36 is therefore allowed to freely rotate around the fixation pin 32, while the two tibia pins 26, 28 are firmly fixed in the rigid connecting bar or block 12 by the setscrews 34. Clinical experience has been limited, but success has been universal, with all patients bearing weight within four days, and fully weight bearing by ten days. Implants are maintained until scar tissue ultimately provides joint stability. No primary repair of the ligaments is performed.

A specific procedure or method of using the device for a tibia-tarsal luxation is as follows: (1) The injured patient is placed in dorsal recumbency; (2) The injured leg is hung for standard orthopedic extremity preparation; (3) A limited approach is performed on the medial aspect of the tibia-tarsal bone to allow only enough exposure to determine the center of rotation of the tibia; (4) A non-threaded pin is passed at the center-of-rotation from medial to lateral; (5) The non-threaded pin is replaced with an enhanced profile end-threaded pin 32 without the requirement for a setscrew; (6) The block 12 is placed on pin 32; (7) The tibio-tarsal joint 40 is reduced to minimize joint space; (8) Two non-threaded pins are placed through the paired throughbores 30 and into the distal tibia; (9) The block 12 and the non-threaded tibial pins are removed and the pins replaced with the pair of threaded tibia pins 26 and 28; (10) The block 12 is replaced on the pins 26 and 28 and the setscrews 34 are tightened; (11) post-operative radiographs are performed to document the positions of the fixation pins 26, 28 and 32; (12) A soft padded bandage is placed on the orthopedic device 10 and the affected region to manage concomitant soft-tissue injuries; (13) Weekly examinations are performed to assess the orthopedic fixation device 10 with its pins 26, 28 and 30; and (14) After four weeks, the block 12 is removed, leaving the pins, under sedation to assess stability of the joint. If adequate stabilization has been achieved, the fixation pins are removed and a soft bandage is placed over the wound.

The advantages accruing through this procedure using this device are as follows: (1) only enough approach to allow determination of the center of rotation is required; (2) The application of the device is rapid; (3) Early weight-bearing is realized in cases of multiple orthopedic injuries; (4) The device allows very stable fixation; (5) The device can be removed for determination of stability prior to final removal of the device; (6) There is no limitation on the range of motion when the device is properly applied; (7) The device is radio-lucent to allow accurate determination of the pin position on post-operative radiographs; (8) The device is steam auto-clavable; (9) The device is reusable; (10) No implants are left in place after the device is removed; (11) There is ease of application in shear injuries, and allows continued bandage changes; and (12) Only a single application of the device is required for both medial and lateral collateral ligament disruption.

Interference with the medial malleolus does not appear to be an issue, although this may need to be addressed in the future. There is potential application for other hinge joints such as the shoulder, elbow, carpus, and stifle. The orthopedic fixation device 10 can be supplied in three sizes for small, medium and large patients. Standard IMEX (™) enhanced profile interface pins are respectively utilized for different sized patients such as lengths of 3/32 inch, 1/8 inch and 5/32 inch. The smallest sized pin can also be used with miniature interface pins such as 0.062 inch and 3/32 inch for cats.

CASE EXAMPLE I

A four year old beagle was injured by a vehicle resulting in multiple injuries including bilateral iliac shaft fractures, and left medial and lateral collateral ligament injuries. Pelvic fractures were repaired, and an orthopedic fixture device 10 was affixed to the tibio-tarsal luxation. The metatarsal fractures were addressed using external coaptation. At four days after surgery, the beagle returned for a bandage change and was fully ambulatory on the tibio-tarsal luxation leg, but was partially weight-bearing on the metatarsal fracture leg. After three weeks, the beagle's wounds have fully healed.

CASE EXAMPLE 2

A three year old German shepherd dog was injured in an attack by canine housemates 8 months earlier, and had a complete luxation of the tibio-tarsal joint. The orthopedic fixture device 10 was then applied resulting in full weight-bearing condition one week later. The device 10 was removed 8 weeks later. Eight months after surgery, the patient had no perceivable lameness, except after strenuous exercise. Radiographs revealed moderate degenerative joint disease.

CASE EXAMPLE 3

Another three year old German shepherd dog sustained a medial collateral ligament rupture when hit by a vehicle. The orthopedic fixture device 10 was applied. The next day, the dog began bearing weight on the injured limb. One week later, the dog limb was fully weight-bearing. The device 10 was removed eight weeks later, resulting in a partial weight-bearing status for several days, and the dog began a rapid recovery. Eight months after surgery, the dog has fully recovered with no evidence of lameness.

Thus, this orthopedic fixation device has shown with concrete examples to accelerate the recovery of animal injuries of bone joints.

It is to be understood that the present invention is not limited to the embodiment described above, but encompasses any and all embodiments within the scope of the following claims.

I claim:

1. A medical device to correct instability of hinged joints comprising:
   a rectangular block including a top planar surface and a bottom planar surface, said block having a first throughbore, a second throughbore adjacent the first throughbore and a third throughbore spaced apart from the first and second throughbores, each said throughbore being aligned and extending from the top to the bottom surface of said block;
   a first elongated fixation pin and a second elongated fixation pin of substantially equal lengths, each said first fixation pin and said second fixation pin having a threaded section proximate a distal end and an unthreaded section proximate a proximal end, the unthreaded section of each said first and second fixation pin being respectively secured within the first and second throughbores of said block by a setscrew; and
   a third elongated fixation pin having a distal end, a proximal end and a length substantially equal to the lengths of said first and second fixation pins, said third fixation pin further having a threaded section proximate the distal end and an unthreaded section proximate the proximal end, the unthreaded section of said third fixation pin being pivotably rotatable within the third throughbore of said block;
   whereby two neighboring bones of a hinged joint can be connected by the medical device and allow rotation of one bone.

2. The device according to claim 1, wherein each said setscrew is made of material selected from the group consisting stainless steel and chromium plated steel.

3. The device according to claim 1, wherein the block has rounded corners.

4. The device according to claim 1, wherein the block is supplied in at least three sizes, and said first, second and third fixation pins range in length from 3/32 inch to 5/32 inch.

5. The device according to claim 1, wherein the block is made of material selected from the group consisting of polymers, aluminum and stainless steel.

6. A method to correct instability in a hinge joint comprising the steps of:
   making a surgical incision in an injured hinge joint region;
   passing a non-threaded pin at the center-of-rotation from medial to lateral of the rotating bone;
   providing a rectangular block having three aligned throughbores with one of the throughbores being separated from the other two throughbores;
   inserting a first threaded fixation pin into the separated throughbore of the block and into a center of rotation of a rotating bone; and
   inserting a second and a third threaded fixation pin in throughbores in the block and into a non-rotating joint bone;
   wherein the first threaded fixation pin pivotally rotates within the separated throughbore of the block, thereby allowing the rotating bone to freely rotate during recovery.

7. The method according to claim 6, wherein a postoperative radiograph is performed to document the positions of the fixation pins.

8. The method according to claim 6, wherein after a suitable period, the block is removed leaving the pins inserted in the hinge joint.

* * * * *